United States Patent [19]
Borgmeier et al.

[11] Patent Number: 6,090,107
[45] Date of Patent: Jul. 18, 2000

[54] RESPOSABLE ELECTROSURGICAL INSTRUMENT

[75] Inventors: Paul R. Borgmeier, Salt Lake City; James D. Isaacson, Sandy; William A. Miller, Bluffdale, all of Utah

[73] Assignee: MegaDyne Medical Products, Inc., Draper, Utah

[21] Appl. No.: 09/175,855

[22] Filed: Oct. 20, 1998

[51] Int. Cl.$^7$ ................................................ A61B 18/14
[52] U.S. Cl. ...................... 606/41; 606/45; 606/46; 606/49
[58] Field of Search ............ 606/41, 42, 44–46, 606/48–50

[56] References Cited

U.S. PATENT DOCUMENTS

| | | | |
|---|---|---|---|
| D. 289,084 | 3/1987 | Freitag | D24/28 |
| D. 377,524 | 1/1997 | Lipp | D24/144 |
| 1,713,970 | 5/1929 | Lowry et al. | 606/45 |
| 1,916,722 | 7/1933 | Ende | 128/303.17 |
| 2,102,270 | 12/1937 | Hyams | 128/303.17 |
| 2,447,169 | 8/1948 | De Sousa . | |
| 3,799,168 | 3/1974 | Peters | 128/303.14 |
| 4,014,343 | 3/1977 | Esty | 128/303.14 |
| 4,074,718 | 2/1978 | Morrison, Jr. | 128/303.14 |
| 4,161,950 | 7/1979 | Doss et al. | 128/303.14 |
| 4,359,052 | 11/1982 | Staub | 128/303.1 |
| 4,411,657 | 10/1983 | Galindo | 604/274 |
| 4,427,006 | 1/1984 | Nottke | 128/303.14 |
| 4,534,347 | 8/1985 | Taylor | 128/303.1 |
| 4,545,375 | 10/1985 | Cline | 128/303.14 |
| 4,562,838 | 1/1986 | Walker | 128/303.14 |
| 4,589,411 | 5/1986 | Friedman | 128/303.14 |
| 4,593,691 | 6/1986 | Lindstrom et al. | 128/303.14 |
| 4,622,966 | 11/1986 | Beard | 128/303.14 |
| 4,640,279 | 2/1987 | Beard | 128/303.14 |
| 4,657,016 | 4/1987 | Garito et al. | 128/303.13 |
| 4,674,498 | 6/1987 | Stasz | 128/303.14 |
| 4,785,807 | 11/1988 | Blanch | 128/303.14 |
| 4,785,808 | 11/1988 | Cary, III | 606/44 |
| 4,862,890 | 9/1989 | Stasz et al. | 128/303.14 |

(List continued on next page.)

FOREIGN PATENT DOCUMENTS

| | | |
|---|---|---|
| 2 592 575 | 7/1987 | France . |
| 2 404 764 | 9/1974 | Germany . |
| 2 120 553 | 12/1983 | United Kingdom . |
| 82/02488 | 8/1982 | WIPO . |

OTHER PUBLICATIONS

Pearce, John A., Ph.D., *Electrosurgery*, Chapman and Hall Ltd., London, pp. 44–61, © 1986.

*Primary Examiner*—Lee Cohen
*Attorney, Agent, or Firm*—Workman, Nydegger & Seeley

[57] ABSTRACT

An improved electrosurgical instrument is disclosed and claims which includes a reusable electrode shaft, a disposable tip and a novel, insulated coupling for removably connecting the disposable tip to the electrode shaft. The present invention provides several advantages and features. The coupling provides ease in connecting the disposable tip to the reusable electrode shaft in an operating room environment. Once the tip is connected to the shaft, the coupling ensures a rigid and secure connection between the tip and the shaft, such that the coupled tip/shaft assembly feels to the surgeon like a single, unitary instrument. In addition, the coupling ensures a good electrical connection between the tip and the shaft, prevents the tip from inadvertently or accidentally becoming separated from the reusable electrode shaft, and maintains the position of the tip relative to the shaft by preventing the tip from rotating relative to the holder. The coupling also includes an insulating sheath that eliminates any conduction paths between the patient and the electrosurgical instrument other than the surgical tip.

17 Claims, 4 Drawing Sheets

U.S. PATENT DOCUMENTS

| | | | |
|---|---|---|---|
| 4,876,110 | 10/1989 | Blanch | 427/2 |
| 4,919,129 | 4/1990 | Weber, Jr. et al. | 606/42 |
| 4,936,842 | 6/1990 | D'Amelio et al. | 606/42 |
| 5,030,218 | 7/1991 | Alexander | 606/45 |
| 5,089,002 | 2/1992 | Kirwan, Jr. | 606/50 |
| 5,100,402 | 3/1992 | Fan | 606/41 |
| 5,195,959 | 3/1993 | Smith | 604/34 |
| 5,197,962 | 3/1993 | Sansom et al. | 606/45 |
| 5,261,906 | 11/1993 | Pennino et al. | 606/46 |
| 5,312,401 | 5/1994 | Newton et al. | 606/46 |
| 5,380,320 | 1/1995 | Morris | 606/33 |
| 5,480,398 | 1/1996 | Eggers | 606/29 |
| 5,496,315 | 3/1996 | Weaver et al. | 606/41 |
| 5,531,743 | 7/1996 | Nettekoven et al. | 606/41 |
| 5,540,684 | 7/1996 | Hassler, Jr. | 606/40 |
| 5,643,256 | 7/1997 | Urueta | 606/45 |
| 5,693,050 | 12/1997 | Speiser | 606/41 |
| 5,697,926 | 12/1997 | Weaver | 606/41 |
| 5,702,387 | 12/1997 | Arts et al. | 606/45 |
| 5,718,714 | 2/1998 | Livneh | 606/205 |
| 5,846,237 | 12/1998 | Nettekoven | 606/41 |
| 5,891,139 | 4/1999 | Cary, III | 606/44 |
| B1 4,785,807 | 7/1996 | Blanch | 606/45 |

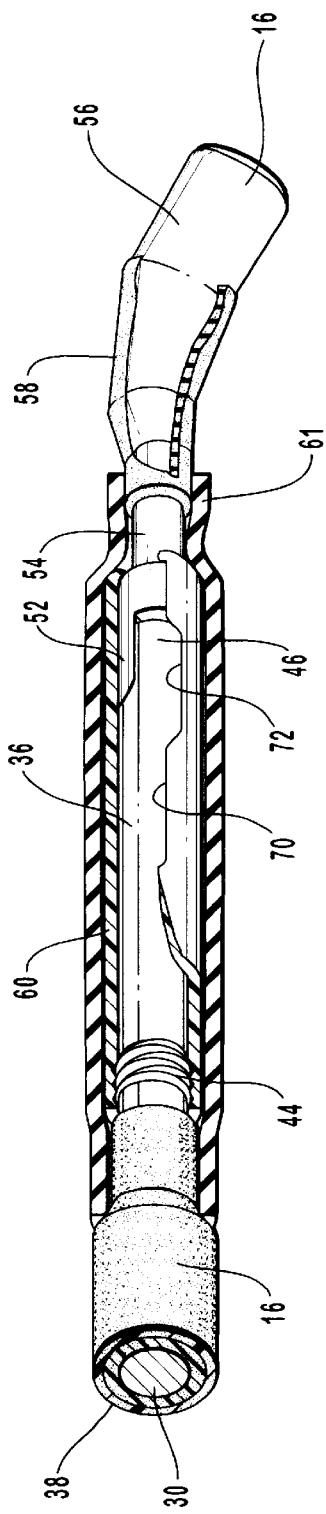
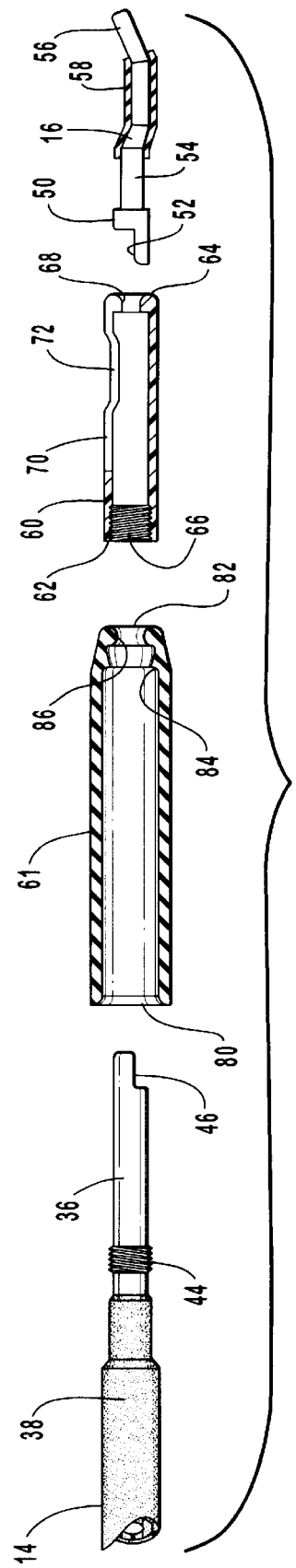
FIG. 3
FIG. 4

RESPOSABLE ELECTROSURGICAL INSTRUMENT

FIELD OF THE INVENTION

This invention relates to surgical instruments having a reusable component and a disposable component securely coupled to the reusable component. In particular, the present invention relates to electrosurgical instruments having reusable electrode extension shafts and disposable tips. The invention has broad application to electrosurgical instruments, both monopolar and bipolar, used in open or minimally invasive procedures.

BACKGROUND OF THE INVENTION

As surgical knowledge and techniques have progressed, there has been a corresponding trend toward size reduction of surgical incisions and invasive instruments, thus decreasing patient trauma and contributing to rapidity of patient recovery. This has led to the practice of laparoscopic and other surgical procedures using small medical electrodes. The incidence of AIDS and other highly dangerous or fatal communicable diseases has highlighted the importance of using either discardable components or of thoroughly sterilizing those that are used more than once.

To protect against the spread of disease, while at the same time reducing the overall cost of surgical equipment, a variety of electrosurgical techniques and implements have heretofore been proposed, illustrative of which are those described in U.S. Pat. No. 1,916,722 to Ende, issued Jul. 4, 1933; German Patent Application 2,404,764 to Weissman et al., published Sep. 19, 1974; U.S. Pat. No. 5,531,743 to Nettekoven et al, issued Jul. 2, 1996; U.S. patent application Ser. No. 08/547,571 by Nettekoven, filed Oct. 24, 1995; PCT International Application No. 82/0084, filed on Jan. 25,1982 by William S. Walker; and PCT International Application No. 91/05520 filed on Aug. 2, 1991 by Edwin Langberg. According to proposals of these patents, multi-element implements have included reusable bodies with removable and disposable tips or electrodes. The main bodies or holders may be sterilized if needed and re-used, and the tips, blades or electrodes may be discarded after a single use or sterilized and re-used.

The multi-element electrosurgical instruments found in the prior art, however, generally suffer from some significant limitations and drawbacks. For example, some of the devices found in the prior art include a relatively simple press-fit or frictional connection between a disposable tip and a reusable electrode shaft, which has several disadvantages. First, such a connection may allow the tip to become inadvertently separated from the shaft during a surgical procedure, which poses a danger to the patient and may require further and even more invasive surgical procedures to retrieve the separated tip. Another limitation is that such a connection may permit the tip to rotate relative to the shaft during use. Because many electrosurgical tips are asymmetrical, fixing the position of the tip relative to the shaft assists the physician in properly orienting the tip during a surgical procedure, thereby enabling the surgeon to more precisely position the surgical tip at the desired surgical location of the patient during a procedure. Further, many devices found in the prior art suffer from the fact that the tip is often not rigidly secured to the end of the shaft. It will be appreciated that the feel of the instrument in the hand of the surgeon is extremely important and that any play in the connection between the disposable tip and the shaft is, therefore, undesirable. Further still, many of the devices found in the prior art do not adequately insulate the connection between the shaft and the tip so as to guard against the possibility of exposing electrically conductive surfaces, which may come into contact with the patient during a procedure, provide an unintended conduction path to the patient, and result in inadvertent burns or cuts in the vicinity of the surgical site. This is of particular concern in relation to electrosurgical instruments adapted for laparoscopic procedures, where such unintended burns or cuts may occur outside of the limited field of vision afforded the surgeon by the laparoscope. Accordingly, there has continued to be a need for an improved resposable electrosurgical instrument comprising a reusable electrode shaft, a disposable tip and an improved coupling therebetween, which overcomes these limitations and disadvantages.

BRIEF SUMMARY AND OBJECTS OF THE INVENTION

The improved resposable electrosurgical instrument according to the present invention includes a reusable electrode shaft, a disposable tip and a novel, insulated coupling for removably connecting the disposable tip to the electrode shaft. The present invention provides several advantages and features. The coupling provides ease in connecting the disposable tip to the reusable electrode shaft in an operating room environment. Once the tip is connected to the shaft, the coupling ensures a rigid and secure connection between the tip and the shaft, such that the coupled tip/shaft assembly feels to the surgeon like a single, unitary instrument. Significantly, the coupling of the present invention is designed so that manipulation by the surgeon during use of the instrument will not result in the tip accidentally separating from the shaft. In addition, the coupling ensures a good electrical connection between the tip and the shaft, prevents the tip from inadvertently or accidentally becoming separated from the reusable electrode shaft, and maintains the position of the tip relative to the shaft by preventing both rotational and longitudinal movement of the tip relative to the shaft and vice versa. Further still, the coupling is self-aligning in the sense that it will not permit the tip to be coupled to the shaft unless and until the respective elements are in proper alignment, yet it does not require the surgeon to visually inspect and align the respective elements.

The coupling also includes a protective sheath that electrically insulates the conductive surfaces of the coupling so as to prevent and eliminate any unintended conduction paths between the patient and the electrosurgical instrument other than at the surgical tip. In addition, the protective sheath provides an effective fluid seal around the mechanical elements of the coupling thereby preventing the accumulation of contaminants and other biohazards.

It is an object of the invention to improve electrosurgical implements. Other objects of the invention are: to provide an improved resposable electrosurgical instrument having a reusable main body portion or shaft and a disposable tip; to provide an improved coupling mechanism for connecting a disposable electrosurgical tip to a reusable electrode shaft; to provide an improved resposable electrosurgical instrument having a reusable electrode extension shaft and a disposable tip that guards against and prevents the disposable tip from inadvertently or unintentionally becoming unattached or decoupled from the reusable electrode extension shaft during normal use and manipulation; to provide an improved resposable electrosurgical instrument having a reusable electrode extension shaft and a disposable tip that is self-aligning and maintains and preserves the orientation and alignment of the tip relative to the shaft; to provide an improved resposable electrosurgical instrument having a reusable electrode extension shaft and a disposable tip that guards against and prevents any unintended electrical conduction paths between the instrument and the patient other than at the intended surgical tip; and to provide an improved resposable electrosurgical instrument that facilitates the use of coated electrosurgical tips, which are typically disposable, in combination with reusable electrode extension shafts.

Additional objects and advantages of the invention will be set forth in the description which follows, and in part will be obvious from the description, or may be learned by the practice of the invention. The objects and advantages of the invention may be realized and obtained by means of the instruments and combinations set forth in the following description and particularly pointed out in the appended claims.

BRIEF DESCRIPTION OF THE DRAWING

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and, therefore, are not to be considered limiting of its scope, the invention will be described and explained with additional specificity and detail through the use of the accompanying drawings in which:

FIG. 3 is a perspective view of the end portion of the electrosurgical instrument of the present invention, with portions of the insulating outer sheath and portions of the inner plastic sleeve cut-away to show the mating portions of the tip and the shaft in mating relationship;

FIG. 4 is an exploded, cross-sectional side view of the electrosurgical instrument of the present invention, taken along cutting plane lines 4—4 of FIG. 2.

DETAILED DESCRIPTION OF A PREFERRED EMBODIMENT

Before proceeding to a detailed description, it may be helpful to define the term "resposable". As used herein, "resposable" means a device in which a component, such as a surgical tip or blade, is optionally disposable and in which one or more other components, such as a holding member for the optionally disposable part, is reusable.

Figure 1:
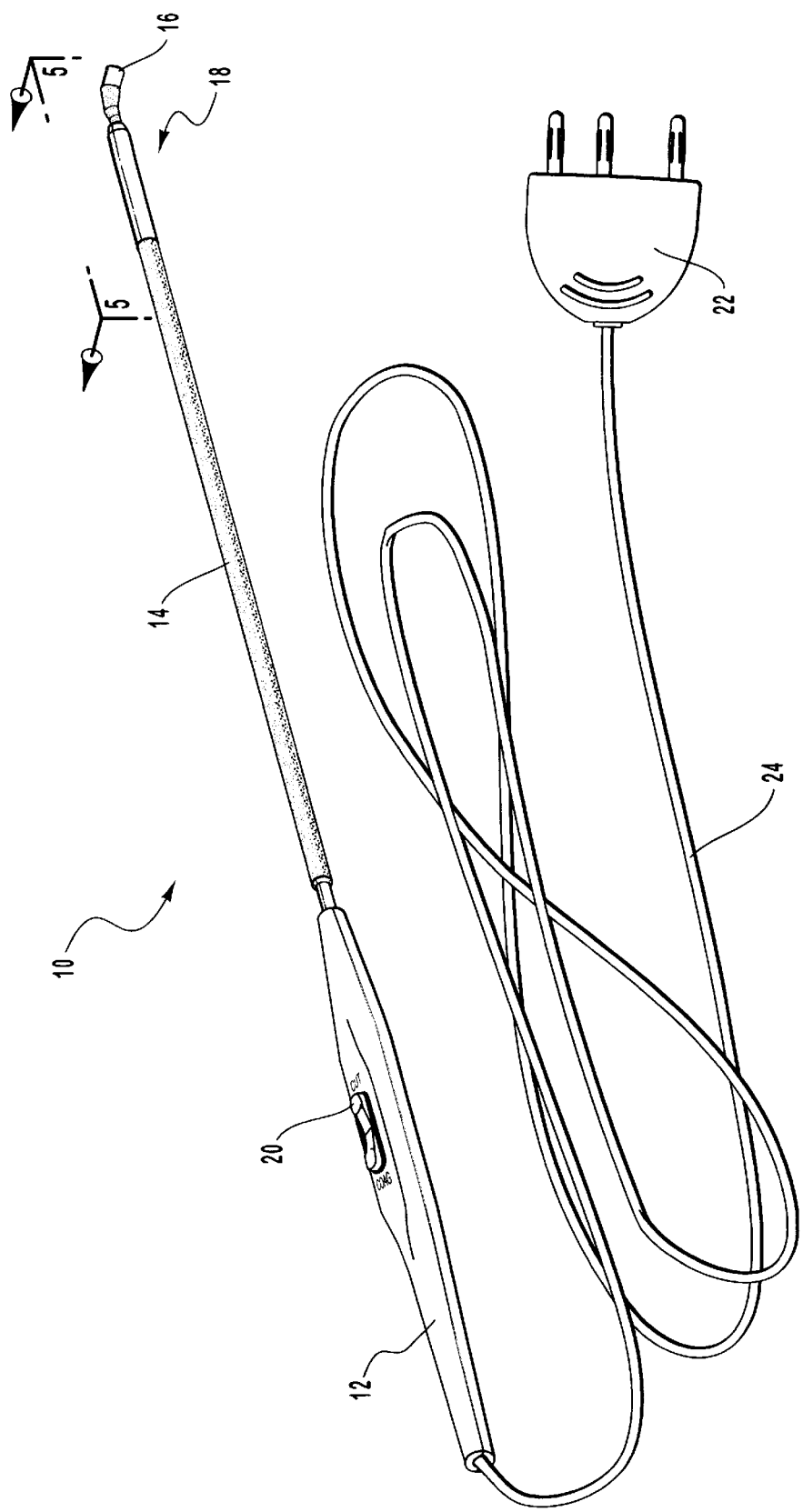
FIG. 1 is a perspective view of a electrosurgical instrument in accordance with the invention.

Now turning to the drawing, and particularly FIG. 1 thereof, it will be seen to be a perspective view of the an electrosurgical assembly in accordance with the present invention, generally designated by reference numeral 10. Electrosurgical assembly 10 consists generally of a hand-held wand or pencil 12, an elongated extension shaft or electrode 14, a disposable electrosurgical tip 16, and a means for selectively coupling tip 16 to shaft 14, which coupling means is generally designated at 18. Shaft 14, tip 16 and coupling means 18 may sometimes be collectively referred to herein as the "electrosurgical instrument." Pencil 12 is preferably provided with an actuator switch 20 for selectively applying RF energy through the tip 16 to the desired surgical site on a patient. RF energy is provided to the pencil 12 from a suitable electrosurgical unit (not shown) through a connector 22 and wire 24. Although switch 20 is shown as being located on pencil 12, a foot switch could also be used as well as any other means for selectively applying electrical energy to the electrosurgical instrument.

Figure 2:
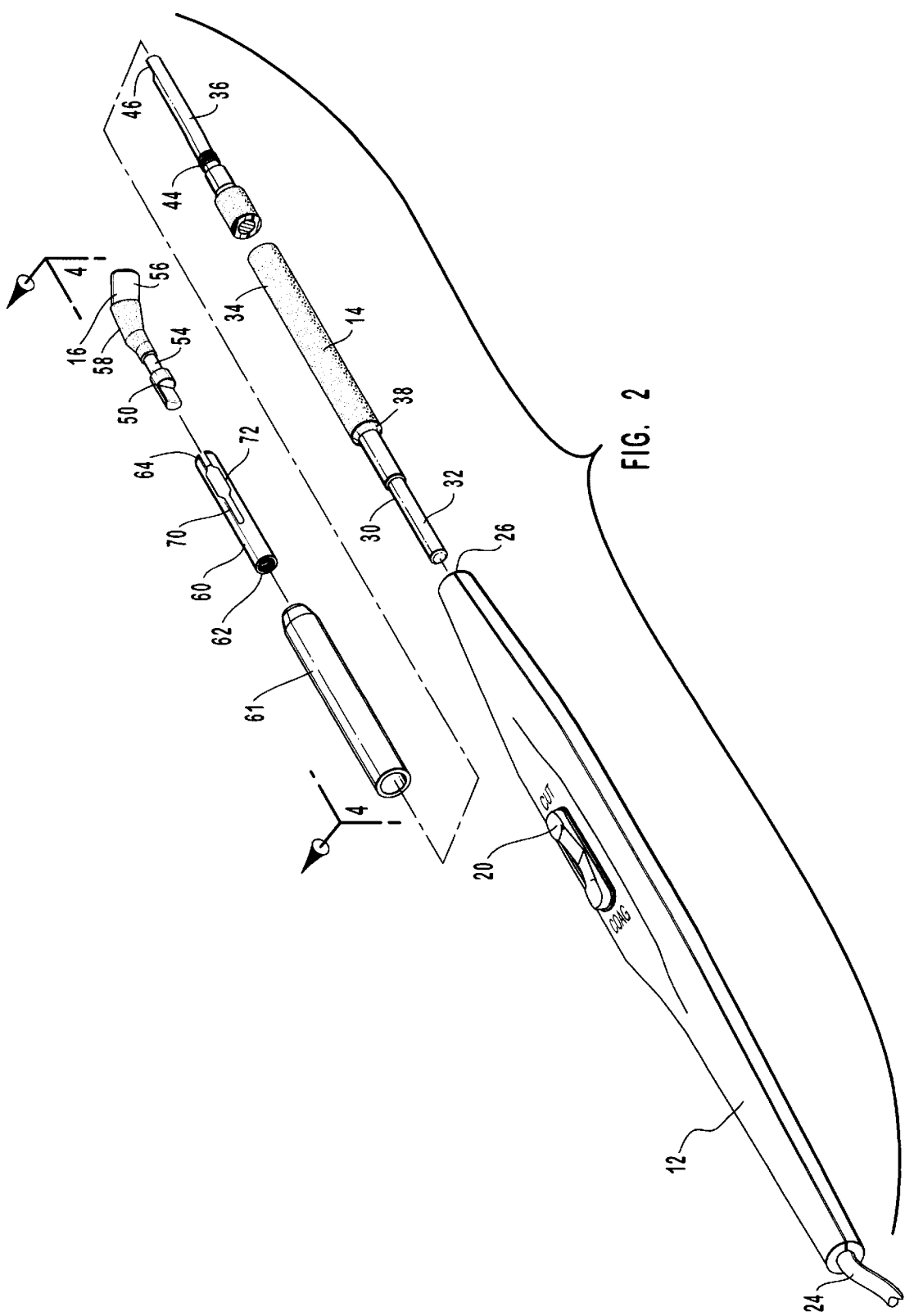
FIG. 2 is an exploded perspective view of the electrosurgical instrument of FIG. 1.
Figure 5:
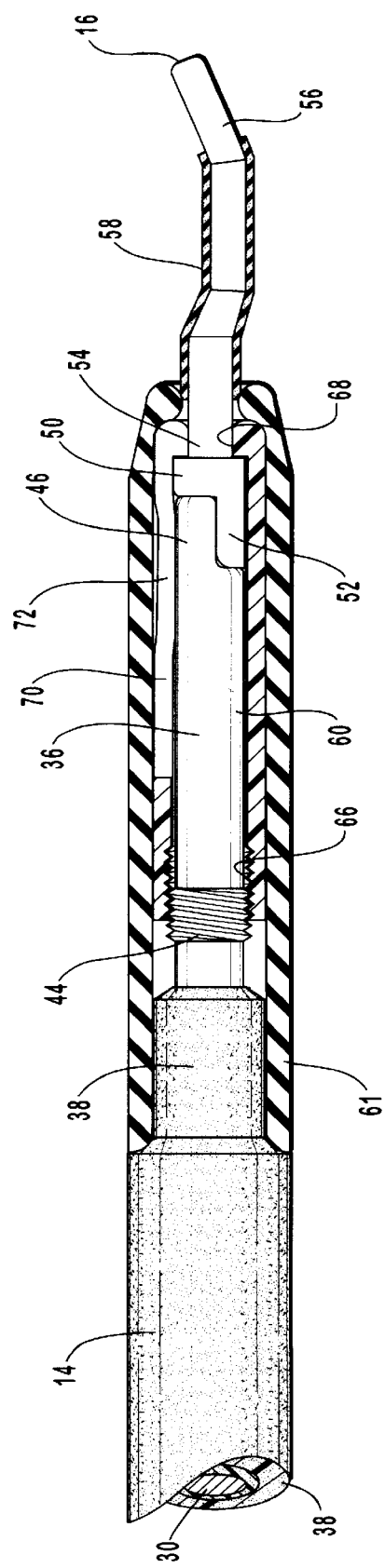
FIG. 5 is an assembled, cross-sectional side view of the electrosurgical instrument of the present invention, taken along cutting plane lines 5—5 of FIG. 1.

Referring to FIG. 2 and as described in more detail below, pencil 12 has a cylindrical recess 26 in its distal end, configured to receive the proximal end of shaft 14 in mating relationship. It will be readily understood by those skilled in the art that a conductive material is located about at least a portion of the inner wall of cylindrical recess 26, which conductive material is electrically coupled to the output leg or pole of actuator switch 20.

Referring generally to FIGS. 2 and 4, shaft 14 consists of an elongated, electrically conductive metal rod 30, having a proximal end portion 32, a major body portion 34, and distal end portion 36. Major body portion 34 is covered with a suitable insulating material 38. In one presently preferred embodiment, insulating material 38 consists of two concentric layers of insulating material having contrasting colors as more particularly described in U.S. Pat. No. 5,531,743 to Nettekoven et al., the disclosure of which is incorporated herein by reference. Insulating material 38 terminates at proximal end portion 32 and distal end portion 36 of shaft 14, such that conductive portions measuring approximately one inch in length are exposed at proximal and distal end portions 32 and 36. As alluded to above, the exposed conductive surface of proximal end portion 32 engages cylindrical recess 26 of pencil 12 in mating relationship. The relative dimensions of proximal end portion 32 and cylindrical recess 26 are such that cylindrical recess 26 receives the proximal end portion 32 in a close tolerance, frictional connection, thereby providing an electrical coupling between pencil 12 and shaft 14. As best illustrated in FIG. 4, distal end portion 36 has an external threaded portion 44 located adjacent to the distal end of insulating material 38. Distal end portion 36 also terminates in a keyway 46 located at its extreme distal end. The purposes and functions of threaded portion 44 and keyway 46 will be discussed in detail below.

With continued reference to FIGS. 2 and 4, it will be seen that tip 16 consists of an end portion 50 having a keyway 52 at its proximal end, a neck portion 54 having a reduced cross section, and a blade or working end portion 56 located at its distal end. Furthermore, portions of neck portion 54 and blade portion 56 are covered with a suitable electrically insulative material 58. In addition, in one presently preferred embodiment, blade portion 56 is preferably coated with a suitable non-stick coating as more particularly described in U.S. Pat. Nos. 4,785,807 and 4,876,110 to Blanch, the disclosures of which is incorporated herein by reference. In the illustrated embodiment, tip or blade portion 56 is shown as having a relatively blunt, flat and angled configuration. However, it should be understood and appreciated that any shape or configuration of electrosurgical tip can be used with the present invention and that the particular shape or configuration of the tip is not central to this invention, but is shown for illustrative purposes only, and is not intended to limit the scope of the present invention.

As discussed in more detail below, keyways 46 and 52 are configured to complementarily engage one another as shaft 14 and tip 16 are coupled together. Once securely coupled together in the manner described below, keyways 46 and 52 cooperate to provide an electrical coupling between shaft 14 and tip 16. In addition, keyways 46 and 52 cooperate to prevent rotational movement of tip 16 relative to shaft 14 and vice versa.

The resposable electrosurgical instrument of the present invention also includes a sleeve 60 and a sheath or overboot 61. In one presently preferred embodiment, sleeve 60 is preferably made from a suitable rigid medical grade plastic, such as polycarbonate, but it could also be made from any other suitable material, such as metal, ceramics, etc. Sheath or overboot 61 is preferably made from a suitable electrically insulative, yet flexible medical grade elastomer. As best illustrated in FIGS. 2 and 4, sleeve 60 is of a generally cylindrical cross section, having a proximal end 62 and a distal end 64. At its proximal end 62, sleeve 60 includes internal threads 66, which are configured complementarily to engage the external threads 44 of shaft 14. At its distal end 64, sleeve 60 includes a collar 68 having a reduced inner diameter that approximates the outer diameter of neck portion 54 of tip 16. As best shown in FIG. 2, sleeve 60 also includes a longitudinal slot 70, which extends along approximately one-half the length of sleeve 60, beginning approximately at the midpoint of sleeve 60 and extending through collar 68 and the distal end 64 of sleeve 60. As further illustrated in FIG. 2, slot 70 includes a widened portion 72 adjacent collar 68.

As best seen in FIG. 4, sheath or overboot 61 is generally tubular in shape and has a proximal end 80 and a distal end 82. The internal diameter of overboot 61 is approximately the same or slightly smaller than the external diameter of sleeve 60 so as to permit sleeve 60 to be inserted into and engage the interior surface of overboot 61 in a generally press fit relationship. Overboot 61 terminates at its distal end 82 in an inner collar 84 and an outer collar 86. Inner collar 84 is configured and dimensioned to snugly fit around the distal end 64 of sleeve 60 once sleeve 60 is inserted into overboot 61. Outer collar 86 is configured and dimensioned to snugly fit around the outside surface of the insulating material 58 of tip 16 (as illustrated in FIG. 3) once the electrosurgical instrument is fully assembled in the manner described below.

Together, tip 16, sleeve 60 and sheath 61 form a disposable electrosurgical tip assembly. In accordance with one presently preferred aspect of the invention, tip 16, sleeve 60 and overboot 61 will be preassembled and sold as a single, disposable unit, whereas extension shaft or electrode 14 may be resterilized and reused for multiple procedures, thereby reducing the equipment cost and, thus, the overall cost of performing laparoscopic procedures. To assemble the tip assembly of the present invention, end portion 50 of tip 16 is inserted through widened portion 72 of slot 70 formed in sleeve 60 and the neck portion 52 of tip 16 is positioned within collar 68 of sleeve 60. It will be appreciated that, though relatively rigid, sleeve 60 has sufficient flexibility that sleeve can be temporarily deformed so as to permit end portion 50 of tip 16 to be inserted through widened portion 72 of slot 70 and to be positioned within sleeve 60. Once the end portion 50 and neck portion 52 have been positioned within sleeve 60 in this manner, flexible sheath or overboot 61 is positioned over and around sleeve 60 and an intermediate portion of tip 16, which is best illustrated in FIG. 3.

The present invention also provides means for selectively and securely coupling tip 16 to the distal end of shaft 14. In one presently preferred embodiment, the coupling means consists of means for aligning and maintaining the relative positions of tip 16 and shaft 14, means for selectively and removably fastening tip 16 to shaft 14, and means for sealing and electrically insulating the coupling means.

In the illustrated embodiment, which is simply illustrative of one presently preferred embodiment of the present invention, the structure corresponding to the aligning and maintaining means is keyway 46 of shaft 14 in cooperation with keyway 52 of tip 16. While keyways 46 and 52 are described and illustrated as having a generally semi-circular cross section with flat mating surfaces, it will be readily apparent to those skilled in the art that any number of mechanical couplings can be adapted to perform the same or equivalent functions. For example, shaft 14 could terminate in a splined shaft configured to mate with a complementary splined recess formed in the proximal end of tip 16. Any suitable mechanical coupling known in the art that performs the same or equivalent functions of aligning shaft 14 with tip 16 and, thereafter, maintaining the relative aligned positions of shaft 14 and tip 16 is contemplated within the meaning of the term aligning and maintaining means.

In the illustrated embodiment, which, again, is simply illustrative of one presently preferred embodiment of the present invention, the structure corresponding to the fastening means is external threaded portion 44 of shaft 14 in cooperation with internal threaded portion 66 of sleeve 60. While portions 44 and 66 are described and illustrated as having complementary threads that mate with one another, it will be readily apparent to those skilled in the art that any number of mechanical devices can be adapted to perform the same or an equivalent fastening function. For example, instead of using the type of simple threads illustrated in the drawings, the fastening means could also comprise complementary luer fittings formed on shaft 14 and sleeve 60. Similarly, fastening means could comprise a bayonet style connector. Accordingly, any suitable mechanical fastener known in the art that performs the same or the equivalent functions of selectively and removably fastening tip 16 to shaft 14 is contemplated within the meaning of the term fastening means.

In the illustrated embodiment, which, again, is simply illustrative of one presently preferred embodiment of the present invention, the structure corresponding to the sealing and insulating means is overboot 61. While overboot 61 is described and illustrated as being a generally tubular, flexible and resilient elastomer, it will be readily apparent to those skilled in the art that any number of alternative embodiments and structures could be employed to perform the same or equivalent functions. Accordingly, any suitable material and structure known in the art that performs the same or equivalent functions of sealing and electrically insulating the coupling means is contemplated within the meaning of the term sealing and insulating means.

Once tip 16, sleeve 60 and overboot 61 have been assembled in the manner described above, tip 16 may be selectively and removably coupled to shaft 14 by inserting the distal end 36 of shaft 14 into the proximal end of overboot 61 and then into the proximal end of sleeve 60. If necessary, shaft 14 is then rotated relative to tip 16 (or vice versa) until keyways 46 and 52 are properly aligned so as to permit further engagement. Once keyways 46 and 52 are aligned in this manner, shaft 14 can be further inserted into sleeve 60 and overboot 61 until the external threads 44 of shaft 14 begin to engage the internal threads 66 of sleeve 60. Finally, once threads 44 and 66 begin to engage one another, then sleeve 60 and overboot 61 are rotated relative to shaft 14 and tip 16 until threads 44 and 66 are fully engaged with one another and keyways 46 and 52 firmly and securely seated against one another.

The relative dimensions and spacing of the keyways 46 and 52 and threads 44 and 66 are such that threads 44 cannot engage threads 66 unless and until keyways 46 and 52 are properly aligned relative to, and at least minimally engaged with, one another. In this way, the electrosurgical instrument of the present invention is self-aligning, in that tip 16 cannot be coupled to shaft 14 unless and until shaft 14 and tip 16 are properly aligned with one another. Furthermore, the task of aligning shaft 14 and tip 16 does not require the surgeon to visually inspect the instrument and visually align any type of alignment markings provided on the device. Rather, the surgeon simply rotates tip 16 relative to shaft 14 until keyways 46 and 52 come into proper alignment, which the surgeon can detect by feel alone in the form of a slight movement in the longitudinal direction of tip 16 relative to shaft 14 as the leading edges of keyways 46 and 52 begin to engage one another. This longitudinal movement is limited, however, as the leading edge of threads 44 abutts the opposing leading edge of threads 66.

It should be appreciated that the complementary mating surfaces of the keyways 46 and 52 provide a good electrical connection between shaft 14 and tip 16. In addition, once coupled in this manner, keyways 46 and 52 and threaded portions 44 and 66 cooperate to form a secure and rigid connection between shaft 14 and tip 16. Such rigid and secure connection prevents unwanted longitudinal movement of tip 16 relative to shaft 14, thereby maintaining good electrical contact between the respective mating surfaces shaft 14 and tip 16, preventing inadvertent separation of tip 16 from shaft 14 during a surgical procedure, and presenting the feel of a single unitary instrument to the surgeon. At the same time, such rigid and secure connection also prevents unwanted rotational movement of tip 16 relative to shaft 14, thereby maintaining and preserving the orientation of tip 16 relative to shaft 14. Another desirable feature of the foregoing embodiment of coupling means 18 is that it does not require shaft 14, the reusable component, to include any internal geometries, recesses or orifices, which may collect contaminants or other biohazards. Remembering that shaft 14 is intended to be reusable, the configuration of external threads 44 and keyway 46 lend themselves to efficient and effective cleaning and resterilization of shaft 14 between its use in consecutive surgical procedures.

Once fully assembled, the proximal end of overboot 61 is configured to snugly fit over and around a portion of the distal end of the insulative material 38 provided on shaft 14, sleeve 60, and a portion of the intermediate portion of tip 16 as best illustrated in FIG. 3. In this manner, overboot 61 electrically isolates the point at which shaft 14 is electrically coupled to tip 16 from the patient, thereby eliminating any conduction path to the patient except through the intended working portion 56 of tip 16. In addition, overboot 61 provides an effective fluid tight seal, shielding the mechanical coupling elements contained within overboot 61 from a patient's blood, tissue or other biological material.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An improved electrosurgical instrument comprising:
    an elongated electrically conductive shaft having a proximal end portion, an intermediate body portion, and a distal end portion, wherein the intermediate body portion is covered with an electrically insulative material;
    an electrosurgical tip having a proximal end portion, an intermediate body portion, and a distal end portion; and
    means for selectively and securely coupling the tip to the distal end portion of the shaft so as to prevent longitudinal and rotational movement of the electrosurgical tip relative to the shaft, the means substantially continually preventing rotational movement of the tip relative to the shaft until the tip and the shaft are substantially disengaged one from the other.

2. The electrosurgical instrument of claim 1 wherein the coupling means comprises:
    a first means for aligning and maintaining the relative positions of the shaft and the tip formed in the distal end portion of the shaft; and
    a second means for aligning and maintaining the relative positions of the shaft and the tip formed in the proximal end portion of the tip,
    wherein the first and second aligning means are configured so as to mate with one an other in complementary engagement.

3. The electrosurgical instrument of claim 2 wherein said first and second aligning means comprise complementary keyways.

4. The electrosurgical instrument of claim 3 wherein the coupling means further comprises a substantially rigid, generally cylindrical sleeve having a proximal end, an intermediate body portion, and a distal end, wherein the distal end of the sleeve surrounds and is mechanically coupled to the proximal end portion of the tip.

5. The electrosurgical instrument of claim 4 wherein the coupling means further comprises:
    a first means for selectively and removably fastening the sleeve to the shaft formed on the distal end portion of the shaft adjacent to and spaced inwardly from said first aligning means; and
    a second means for selectively and removably fastening the sleeve to the shaft formed in the proximal end of the sleeve,
    wherein the first and second means are configured so as to mate with one another in complementary engagement.

6. The electrosurgical instrument of claim 5, wherein said first fastening means comprises external threads formed on the distal end portion of the shaft, wherein the second fastening means comprises internal threads formed within the proximal end of the sleeve, and wherein the external and internal threads are complementary of one another so as to permit selective threaded engagement and disengagement of one another.

7. The electrosurgical instrument of claim 1, 2, 3, 4, 5 or 6 further comprising means for sealing and electrically insulating the coupling means.

8. The electrosurgical instrument of claim 7, wherein the sealing and insulating means comprises an elongated, generally tubular, electrically insulative and flexibly resilient sheath positioned over and around the coupling means in a substantially close tolerance, press-fit relationship.

9. An improved electrosurgical instrument comprising:
    an elongated electrically conductive shaft having a proximal end portion, an intermediate body portion, and a distal end portion, wherein the intermediate body portion is covered with an electrically insulative material;
    an electrosurgical tip having a proximal end portion, an intermediate body portion, and a distal end portion; and
    a coupling wherein the tip is rigidly secured to the distal end portion of the shaft so as to prevent both longitudinal and rotational movement of the tip relative to the shaft, the coupling substantially continually preventing rotational movement of the tip relative to the shaft until the tip and the shaft are substantially disengaged one from the other.

10. The electrosurgical instrument of claim 9 wherein the coupling further comprises:

a first keyway formed in the distal end portion of the shaft; and a second keyway formed in the proximal end portion of the tip, wherein the first and second keyways are configured so as to mate with one another in complementary engagement.

11. The electrosurgical instrument of claim 10 wherein the coupling further comprises a substantially rigid, generally cylindrical sleeve having a proximal end, an intermediate body portion and a distal end, wherein the distal end of the sleeve surrounds and is mechanically coupled to the proximal end portion of the tip.

12. The electrosurgical instrument of claim 11 wherein the coupling further comprises:

an external threaded portion formed about the distal end portion of the shaft adjacent to and spaced inwardly from the first keyway; and an internal threaded portion formed within the proximal end of the sleeve;

wherein the external and internal threaded portions are configured to mate with one another in complementary engagement.

13. The electrosurgical instrument of claim 12 further comprising an elongated, generally tubular, electrically insulative and flexibly resilient sheath positioned over and around the coupling in a substantially close tolerance, press-fit relationship.

14. An improved electrosurgical instrument comprising:

an elongated electrically conductive shaft having a proximal end portion, an intermediate body portion, and a distal end portion, wherein the intermediate body portion is covered with an electrically insulative material; and a disposable electrosurgical tip assembly, wherein the tip assembly is selectively and removably connected to the distal end portion of the shaft in such a manner that the tip assembly is rigidly secured to the shaft so as to prevent both longitudinal and rotational movement of the tip assembly relative to the shaft and the tip assembly is adapted to substantially continually prevent rotational movement of the tip assembly relative to the shaft until the tip assembly and the shaft are substantially disengaged one from the other.

15. The improved electrosurgical instrument of claim 14 wherein the tip assembly comprises:

an electrically conductive electrosurgical tip having a proximal end portion, an intermediate portion and an exposed working surface at its distal end, wherein the intermediate portion is covered with an electrically insulative material;

an elongated substantially rigid, generally cylindrical sleeve having a proximal end portion, an intermediate body portion and a distal end portion, wherein the distal end portion of the sleeve surrounds and is mechanically coupled to the proximal end portion of the tip; and an elongated, generally tubular, electrically insulative and flexibly resilient sheath positioned over and around the sleeve and the proximal end portion of the tip in a substantially close tolerance, press-fit relationship.

16. The improved electrosurgical instrument of claim 15 wherein the shaft further comprises a first keyway at its distal end, wherein the tip further comprises a second keyway formed in its proximal end, and wherein said first and second keyways are configured so as to mate with one an other in complementary engagement and thereby align the tip with the shaft and prevent rotation of the tip relative to the shaft.

17. The improved electrosurgical instrument of claim 16 wherein the shaft further comprises an external threaded portion formed about the distal end portion of the shaft proximate to and spaced inwardly from the distal end thereof, wherein the sleeve further comprises an internal threaded portion formed within the proximal end portion of the sleeve, and wherein the external and internal threaded portions are configured to mate with one another in complementary engagement and thereby maintain the first and the second keyways in mating engagement and prevent longitudinal movement of the tip relative to the shaft.

* * * * *